(12) United States Patent
Molz et al.

(10) Patent No.: US 8,414,907 B2
(45) Date of Patent: Apr. 9, 2013

(54) COATINGS ON MEDICAL IMPLANTS TO GUIDE SOFT TISSUE HEALING

(75) Inventors: Fred Molz, Collierville, TN (US); Sharonda Felton, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1338 days.

(21) Appl. No.: 11/116,414

(22) Filed: Apr. 28, 2005

(65) Prior Publication Data

US 2006/0246105 A1 Nov. 2, 2006

(51) Int. Cl.
*A61F 2/46* (2006.01)
(52) U.S. Cl. .......................................... 424/423
(58) Field of Classification Search .................... 424/423
See application file for complete search history.

(56) References Cited

U.S. PATENT DOCUMENTS

| | | | |
|---|---|---|---|
| 4,346,108 A | 8/1982 | Singer | |
| 4,603,695 A | 8/1986 | Ikada et al. | |
| 4,672,031 A | 6/1987 | Prockop | |
| 4,704,131 A | 11/1987 | Noishiki et al. | |
| 4,749,585 A * | 6/1988 | Greco et al. | 428/422 |
| 4,781,591 A | 11/1988 | Allen | |
| 4,840,626 A | 6/1989 | Linsky et al. | |
| 4,938,763 A | 7/1990 | Dunn et al. | |
| 5,007,916 A | 4/1991 | Linsky et al. | |
| 5,073,373 A | 12/1991 | O'Leary et al. | |
| 5,134,229 A | 7/1992 | Saferstein et al. | |
| 5,156,839 A | 10/1992 | Pennell et al. | |
| 5,190,759 A | 3/1993 | Lindblad et al. | |
| 5,219,895 A | 6/1993 | Kelman et al. | |
| 5,257,632 A | 11/1993 | Turkel et al. | |
| 5,278,201 A | 1/1994 | Dunn et al. | |
| 5,278,202 A | 1/1994 | Dunn et al. | |
| 5,326,354 A | 7/1994 | Kwarteng | |
| 5,358,973 A | 10/1994 | Lindblad et al. | |
| 5,397,796 A | 3/1995 | Zoeller et al. | |
| 5,412,068 A | 5/1995 | Tang et al. | |
| 5,502,042 A | 3/1996 | Gruskin et al. | |
| 5,505,952 A | 4/1996 | Jiang et al. | |
| 5,508,036 A | 4/1996 | Bakker et al. | |
| 5,509,899 A * | 4/1996 | Fan et al. | 604/103.14 |
| 5,534,524 A | 7/1996 | Bonewald et al. | |
| 5,554,594 A | 9/1996 | Zoeller et al. | |
| 5,583,114 A | 12/1996 | Barrows et al. | |
| 5,612,321 A | 3/1997 | Nguyen | |
| 5,628,781 A | 5/1997 | Williams et al. | |
| 5,652,224 A | 7/1997 | Wilson et al. | |
| 5,658,935 A | 8/1997 | Klingler et al. | |

(Continued)

FOREIGN PATENT DOCUMENTS

| | | |
|---|---|---|
| EP | 0401384 A1 | 12/1989 |
| EP | 1084720 A1 | 3/2001 |

(Continued)

OTHER PUBLICATIONS

Zhu et al., Cells Tissues Organs, 2004, 178, pp. 13-22.*

*Primary Examiner* — Brian Gulledge
(74) *Attorney, Agent, or Firm* — Sorell Lenna & Schmidt LLP

(57) ABSTRACT

Embodiments include coatings or surface treatments for medical instruments, devices, and/or implants that promote soft tissue healing. More particularly, embodiments relate to treating portions of instruments, devices, and implants where tissue healing is desired with tissue healing promoting treatments.

21 Claims, 2 Drawing Sheets

U.S. PATENT DOCUMENTS

| | | | |
|---|---|---|---|
| 5,679,658 A | 10/1997 | Elson | |
| 5,711,958 A | 1/1998 | Cohn et al. | |
| 5,756,145 A | 5/1998 | Darouiche | |
| 5,795,584 A | 8/1998 | Totakura et al. | |
| 5,807,833 A | 9/1998 | Dizerega | |
| 5,846,530 A | 12/1998 | Soon-Shiong et al. | |
| 5,874,109 A * | 2/1999 | Ducheyne et al. | 424/486 |
| 5,874,537 A | 2/1999 | Kelman et al. | |
| 5,931,165 A | 8/1999 | Reich et al. | |
| 5,947,893 A | 9/1999 | Agrawal et al. | |
| 5,962,006 A | 10/1999 | Southard et al. | |
| 5,993,890 A * | 11/1999 | Marchant et al. | 427/2.3 |
| 5,994,133 A | 11/1999 | Meijs et al. | |
| 6,007,833 A | 12/1999 | Chudzik et al. | |
| 6,030,958 A | 2/2000 | Burns et al. | |
| 6,031,069 A | 2/2000 | Oberhoffner et al. | |
| 6,031,148 A | 2/2000 | Hayes et al. | |
| 6,034,088 A | 3/2000 | Reeve et al. | |
| 6,034,140 A | 3/2000 | Schwartz et al. | |
| 6,037,331 A | 3/2000 | Shalaby et al. | |
| 6,063,061 A | 5/2000 | Wallace et al. | |
| 6,074,663 A | 6/2000 | Delmotte et al. | |
| 6,093,388 A | 7/2000 | Ferguson | |
| 6,096,727 A | 8/2000 | Kuo et al. | |
| 6,113,636 A | 9/2000 | Ogle | |
| 6,131,580 A | 10/2000 | Ratner et al. | |
| 6,133,325 A | 10/2000 | Schwartz et al. | |
| 6,136,333 A | 10/2000 | Cohn et al. | |
| 6,139,585 A | 10/2000 | Li | |
| 6,150,581 A | 11/2000 | Jiang et al. | |
| 6,153,252 A | 11/2000 | Hossainy et al. | |
| 6,156,345 A | 12/2000 | Chudzik et al. | |
| 6,162,487 A | 12/2000 | Darouiche | |
| 6,174,855 B1 | 1/2001 | Hansson | |
| 6,217,894 B1 | 4/2001 | Sawhney et al. | |
| 6,231,892 B1 | 5/2001 | Hubbell et al. | |
| 6,235,796 B1 | 5/2001 | Niazi | |
| 6,261,586 B1 * | 7/2001 | McKay | 424/423 |
| 6,280,745 B1 | 8/2001 | Flore et al. | |
| 6,290,729 B1 | 9/2001 | Slepian et al. | |
| 6,294,041 B1 | 9/2001 | Boyce et al. | |
| 6,302,909 B1 | 10/2001 | Ogle et al. | |
| 6,306,922 B1 | 10/2001 | Hubbell et al. | |
| 6,312,725 B1 | 11/2001 | Wallace et al. | |
| 6,313,119 B1 | 11/2001 | Peyman et al. | |
| 6,317,275 B1 | 11/2001 | Yoneyama | |
| 6,328,765 B1 * | 12/2001 | Hardwick et al. | 623/23.72 |
| 6,333,029 B1 * | 12/2001 | Vyakarnam et al. | 424/93.1 |
| 6,350,527 B1 | 2/2002 | Hubbell et al. | |
| 6,352,710 B2 | 3/2002 | Sawhney et al. | |
| 6,372,256 B2 | 4/2002 | Jamiokowski et al. | |
| 6,391,939 B2 | 5/2002 | Tayot et al. | |
| 6,399,264 B1 | 6/2002 | Ogata et al. | |
| 6,410,044 B1 | 6/2002 | Chudzik et al. | |
| 6,410,645 B1 | 6/2002 | Pathak et al. | |
| 6,413,539 B1 | 7/2002 | Shalaby | |
| 6,436,425 B1 | 8/2002 | Henry et al. | |
| 6,440,427 B1 | 8/2002 | Wadstrom | |
| 6,455,541 B1 | 9/2002 | Bonewald et al. | |
| 6,458,889 B1 | 10/2002 | Trollsas et al. | |
| 6,478,822 B1 | 11/2002 | Leroux et al. | |
| 6,486,140 B2 | 11/2002 | Hansson et al. | |
| 6,492,356 B1 | 12/2002 | Peyman et al. | |
| 6,492,494 B1 | 12/2002 | Cederholm-Williams | |
| 6,517,888 B1 | 2/2003 | Weber | |
| 6,521,223 B1 | 2/2003 | Calias et al. | |
| 6,527,938 B2 | 3/2003 | Bales et al. | |
| 6,531,147 B2 | 3/2003 | Sawhney et al. | |
| 6,534,591 B2 | 3/2003 | Rhee et al. | |
| 6,537,979 B1 | 3/2003 | Kuo et al. | |
| 6,548,081 B2 | 4/2003 | Sadozai et al. | |
| 6,551,610 B2 | 4/2003 | Shalaby et al. | |
| 6,552,170 B1 | 4/2003 | Thompson et al. | |
| 6,565,489 B2 | 5/2003 | Ho et al. | |
| 6,566,345 B2 | 5/2003 | Miller et al. | |
| 6,596,267 B1 | 7/2003 | Hubbell et al. | |
| 6,596,338 B2 | 7/2003 | Scott et al. | |
| 6,599,526 B2 | 7/2003 | Dimitrijevich | |
| 6,602,975 B2 | 8/2003 | Hubbell et al. | |
| 6,610,669 B1 | 8/2003 | Calias et al. | |
| 6,613,325 B1 | 9/2003 | Amery et al. | |
| 6,613,432 B2 | 9/2003 | Zamora et al. | |
| 6,630,167 B2 | 10/2003 | Zhang | |
| 6,656,345 B1 | 12/2003 | Chen et al. | |
| 6,673,361 B1 | 1/2004 | Ogura et al. | |
| 6,673,362 B2 | 1/2004 | Calhoun et al. | |
| 6,676,987 B2 | 1/2004 | Zhong et al. | |
| 6,685,956 B2 | 2/2004 | Chu et al. | |
| 6,689,374 B2 | 2/2004 | Chu et al. | |
| 6,689,903 B2 | 2/2004 | O'Meadhra et al. | |
| 6,693,089 B1 | 2/2004 | Li et al. | |
| 6,696,499 B1 | 2/2004 | Cohn et al. | |
| 6,703,041 B2 | 3/2004 | Burns et al. | |
| 6,704,604 B2 | 3/2004 | Soukup et al. | |
| 6,706,780 B2 | 3/2004 | Goldberg et al. | |
| 6,719,960 B1 | 4/2004 | Hills et al. | |
| 6,720,469 B1 | 4/2004 | Curtis et al. | |
| 6,723,709 B1 | 4/2004 | Pressato et al. | |
| 6,726,718 B1 | 4/2004 | Carlyle et al. | |
| 6,736,823 B2 | 5/2004 | Darois et al. | |
| 6,736,849 B2 | 5/2004 | Li et al. | |
| 6,743,463 B2 | 6/2004 | Weber et al. | |
| 6,743,521 B2 | 6/2004 | Hubbell et al. | |
| 6,746,485 B1 | 6/2004 | Zucherman et al. | |
| 6,746,685 B2 | 6/2004 | Williams | |
| 6,749,639 B2 | 6/2004 | Lewallen | |
| 6,749,685 B2 | 6/2004 | Coleman | |
| 6,764,709 B2 | 7/2004 | Flanagan | |
| 6,780,427 B2 | 8/2004 | Baker et al. | |
| 6,790,438 B1 * | 9/2004 | Constancis et al. | 424/78.17 |
| 6,861,088 B2 | 3/2005 | Weber et al. | |
| 7,144,588 B2 | 12/2006 | Oray et al. | |
| 2002/0001584 A1 | 1/2002 | Metner et al. | |
| 2002/0016635 A1 | 2/2002 | Despres, III et al. | |
| 2002/0028181 A1 * | 3/2002 | Miller et al. | 424/43 |
| 2002/0049495 A1 | 4/2002 | Kutryk et al. | |
| 2002/0147486 A1 | 10/2002 | Soukup et al. | |
| 2002/0156529 A1 | 10/2002 | Li et al. | |
| 2002/0168406 A1 | 11/2002 | Goldenberg et al. | |
| 2002/0198601 A1 | 12/2002 | Bales et al. | |
| 2003/0065292 A1 | 4/2003 | Darouiche et al. | |
| 2003/0069354 A1 | 4/2003 | Oyasato et al. | |
| 2003/0073663 A1 | 4/2003 | Wiseman et al. | |
| 2003/0077381 A1 | 4/2003 | Scott et al. | |
| 2003/0094719 A1 | 5/2003 | Yang et al. | |
| 2003/0100739 A1 | 5/2003 | Tsai et al. | |
| 2003/0108659 A1 | 6/2003 | Bales et al. | |
| 2003/0124087 A1 | 7/2003 | Kim et al. | |
| 2003/0133928 A1 | 7/2003 | Metzner et al. | |
| 2003/0170378 A1 | 9/2003 | Wen et al. | |
| 2003/0171825 A1 | 9/2003 | Blunn et al. | |
| 2003/0176927 A1 | 9/2003 | Steinemann et al. | |
| 2003/0180251 A1 | 9/2003 | Friedrich et al. | |
| 2004/0001911 A1 | 1/2004 | Scott et al. | |
| 2004/0009917 A1 | 1/2004 | Redl et al. | |
| 2004/0024081 A1 | 2/2004 | Trieu et al. | |
| 2004/0043016 A1 | 3/2004 | Redl | |
| 2004/0043052 A1 | 3/2004 | Hunter et al. | |
| 2004/0092433 A1 | 5/2004 | Wang et al. | |
| 2004/0115241 A1 | 6/2004 | Calhoun et al. | |
| 2004/0126420 A1 | 7/2004 | Dobbie et al. | |
| 2004/0131754 A1 | 7/2004 | Zitelli et al. | |
| 2004/0141956 A1 | 7/2004 | Oray et al. | |
| 2004/0171545 A1 | 9/2004 | Chaikof et al. | |
| 2004/0185084 A1 | 9/2004 | Rhee et al. | |
| 2004/0249472 A1 | 12/2004 | Liu et al. | |
| 2005/0008620 A1 * | 1/2005 | Shimp et al. | 424/93.7 |
| 2005/0033417 A1 | 2/2005 | Borges et al. | |
| 2005/0171604 A1 | 8/2005 | Michalow | |

FOREIGN PATENT DOCUMENTS

| | | |
|---|---|---|
| EP | 1340476 A1 | 9/2003 |
| WO | WO 90/11092 | 10/1990 |
| WO | 9705238 A1 | 2/1997 |
| WO | WO 97/18904 | 5/1997 |
| WO | WO 97/49434 | 12/1997 |

| | | | | | |
|---|---|---|---|---|---|
| WO | WO 98/50050 | 11/1998 | WO | WO 02/44276 | 6/2002 |
| WO | WO 98/05380 | 12/1998 | WO | WO 03/000344 A1 | 1/2003 |
| WO | WO 99/58186 | 11/1999 | WO | WO 2004/010854 A2 | 2/2004 |
| WO | WO 00/72856 A1 | 12/2000 | WO | WO 2004/021983 A2 | 3/2004 |
| WO | WO 02/17824 | 3/2002 | | | |
| WO | WO 02/17853 A2 | 3/2002 | * cited by examiner | | |

Figure 1
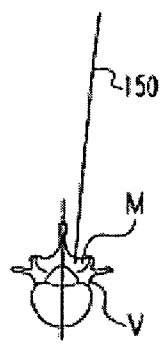
Figure 1a
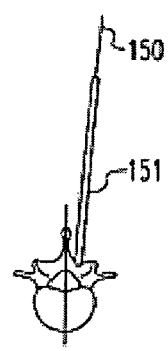
Figure 1b
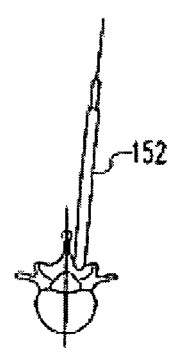
Figure 1c
Figure 1d
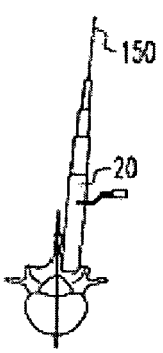
Figure 1e
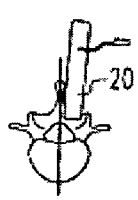
Figure 1f
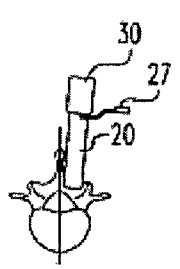
Figure 1g
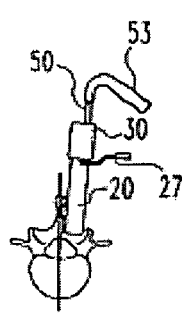
Figure 1h
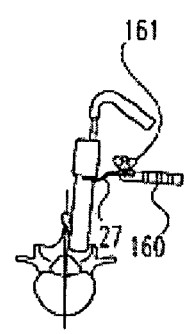
Figure 1i

COATINGS ON MEDICAL IMPLANTS TO GUIDE SOFT TISSUE HEALING

FIELD OF THE INVENTION

Embodiments of the invention relate to coatings and treatments for medical instruments, implants, and devices that assist in guiding soft tissue healing. More particularly, embodiments relate to treating portions of medical implements where tissue healing is desired with tissue healing promoting treatments.

DESCRIPTION OF RELATED ART

Medical implants or prostheses function to replace or augment various structures and tissues in the body. Medical implants include, for example, intervertebral disc replacement devices, spinal fixation systems, facet arthroplasty devices, artificial hips, bone screws, bone plates and rods, prosthetic knee replacements, arterial stents, pacemakers, heart valves, artificial hearts, artificial sphincters, etc. The effectiveness of medical implants sometimes is highly dependent upon the implant's interactions with surrounding tissues, and the ability of the patient to heal after the surgical procedure.

Minimally invasive alternatives such as arthroscopic techniques reduce pain, post-operative recovery time and the destruction of healthy tissue. Orthopedic surgical patients have particularly benefited from minimally invasive surgical techniques. The site of pathology is accessed through portals rather than through a significant incision thus preserving the integrity of the intervening tissues. These minimally invasive techniques also often require only local anesthesia. Avoiding general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with the muscle dissection.

In order to reduce the post-operative recovery time and pain associated with spinal and other procedures, micro-surgical techniques have been developed. For example, in micro-surgical discectomies, the disc is accessed by cutting a channel from the surface of the patient's back to the disc through a small incision. An operating microscope or loupe is used to visualize the surgical field. Small diameter micro-surgical instruments are passed through the small incision and between two laminae and into the disc. The intervening tissues are disrupted less because the incision is smaller. Although these micro-surgical procedures are less invasive, they still involve some of the same complications associated with open procedures, such as injury to the nerve root and dural sac, perineural scar formation, reherniation at the surgical site and instability due to excess bone removal. Suitable minimally invasive procedures for accessing the disc space are disclosed in numerous documents, including, for example, U.S. Pat. Nos. 6,206,822, 6,206,826, 6,200,322, RE37,005, U.S. Pat. Nos. 5,902,231, 5,891,145, 5,885,292, 5,885,291, and 5,741,261, the disclosures of which are incorporated by reference herein in their entirety.

The development of percutaneous spinal procedures has yielded a major improvement in reducing recovery time and post-operative pain because they require minimal, if any, muscle dissection and they can be performed under local anesthesia. For example, U.S. Pat. No. 4,545,374 to Jacobson discloses a percutaneous lumbar discectomy using a lateral approach, preferably under fluoroscopic X-ray. This procedure is limited because it does not provide direct visualization of the discectomy site.

Other procedures have been developed that include arthroscopic visualization of the spine and intervening structures. U.S. Pat. Nos. 4,573,448 and 5,395,317 disclose percutaneous decompression of herniated discs with a posterolateral approach. Fragments of the herniated disc are evacuated through a cannula positioned against the annulus. The '317 patent discloses a biportal procedure which involves percutaneously placing both a working cannula and a visualization cannula for an endoscope. This procedure allows simultaneous visualization and suction, irrigation and resection in disc procedures.

Unfortunately, disadvantages remain with these procedures and the accompanying tools because they are limited to a specific application or approach. For example, many of these references describe a required lateral or a posterolateral approach for percutaneous discectomy. These approaches seek to avoid damage to soft tissue structures and the need for bone removal because it was thought to be impractical to cut and remove bone through a channel. However, these approaches do not address other spinal conditions which may require a mid-line approach, removal of bone or implants.

U.S. Pat. No. 5,439,464 to Shapiro discloses a method and instruments for performing arthroscopic spinal surgeries such as laminectomies and fusions with a mid-line or medial posterior approach using three cannulas. Each of the cannulas requires a separate incision. While Shapiro discloses an improvement over prior procedures which were limited to a posterolateral or lateral approach for disc work, Shapiro's procedure still suffers from many of the disadvantages of known prior percutaneous spinal surgery techniques and tools. One disadvantage of the Shapiro procedure is its requirement of a fluid working space. Another significant detriment is that the procedure requires multiple portals into the patient, thereby increasing tissue injury and pain.

While the minimally invasive surgical techniques and instruments employed to date have been successful in reducing tissue damage and pain, tissue damage and pain still exists. Even small cannula access portals on the order of 5-18 mm in diameter cause damage to the tissue they spread apart, leading to scarring and adhesion formation, which can have an adverse impact on the ability of the implant to function effectively, and have an adverse impact on the efficacy of the surgical procedure itself in the case where an implant is not utilized. This is especially true when the implant is intended to articulate or replace an articulation surface. Adhesions and scarring can severely diminish the usefulness of these implants by adhering to the articulating surface, or preventing or hindering articulation.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY

There is a need for medical implements that ameliorate undesirable interactions between the medical implements on the one hand, and surrounding tissues on the other. There also is a need for methods, instruments, and devices that stimulate advantageous interactions between medical implements on the one hand, and surrounding tissues on the other. Embodiments of the invention solve some or all of these needs, as well as additional needs.

Therefore, in accordance with an embodiment of the present invention, there is provided a medical implement intended to be placed in the body in contact with surrounding body tissue, whereby the medical implement comprises a tissue healing promoting treatment on at least a portion of its surface.

Embodiments also include methods of making the medical implement that include forming the implement, and then modifying at least a portion of its surface to provide a tissue healing promoting treatment on at least a portion of its surface. Embodiments also include methods of performing surgery using the medical instruments, devices, and implants, and devices, as well as kits containing the medical instruments, devices, and implants.

These and other features and advantages of the present invention will be apparent from the description of exemplary embodiments herein.

BRIEF DESCRIPTION OF THE DRAWINGS

FIG. 1(a)-(i) depicts an exemplary set of procedures involved in a surgical method utilizing the medical instruments, devices, and/or implants described herein.

DETAILED DESCRIPTION OF THE PREFERRED EMBODIMENTS

Figure 2:
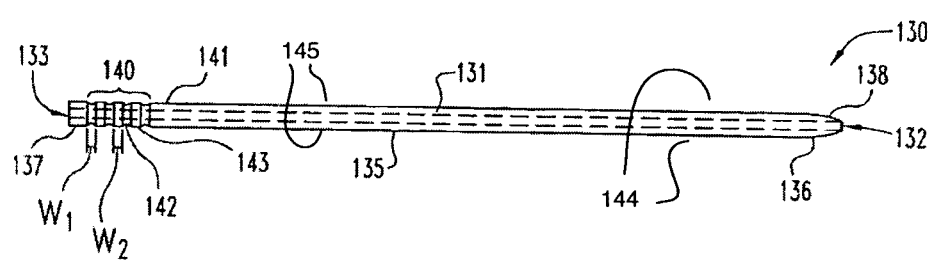
FIG. 2 is an illustration of an exemplary dilator useful in serially dilating tissue to provide an access portal and lumen to an interior position in a patient's body.

The following description is intended to convey a thorough understanding of exemplary embodiments of the invention by providing a number of specific embodiments and details involving surface treatments for promoting selective tissue attachment to medical implants. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments.

For the purposes of promoting an understanding of the embodiments described herein, reference will now be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "an implant" includes a plurality of such implants, as well as a single implant, and a reference to "an anti-adhesion compound" is a reference to one or more compounds and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the various implants, instruments, devices, anti-adhesion agents, tissue healing promoting agents, and other components that are reported in the publications and that might be used in connection with the invention. Nothing herein is to be construed as an admission that the invention is not entitled to antedate such disclosures by virtue of prior invention.

Throughout this description, the expression "tissue healing promoting treatment" denotes any treatment, surface or otherwise, that promotes healing of tissue adjacent the medical implement. Representative tissue healing promoting treatments include coating or impregnating at least a portion of the surface of the respective material with a tissue healing promoting agent, substance, composition, and the like.

Throughout this description, the expression "medical implement" denotes a medical instrument, a medical device, or a medical implant that is intended to contact body tissue. Representative medical implements are described herein. Preferably, the medical implement is a medical instrument, a medical device, and/or a medical implant that is intended to contact body tissue during a surgical procedure performed on a patient's spine.

It is a feature of an embodiment of the invention to provide medical instruments, devices, and/or implants, and to provide a method for promoting tissue healing. Surfaces of the medical instruments, devices, and/or implants, or at least portions thereof, and preferably those surfaces adjacent to which tissue healing is desired, may be treated with a tissue healing promoting treatment.

Any medical instrument, device, and/or implant contain the tissue healing promoting treatments described herein, and preferably, these medical implements are coated with a tissue healing promoting agent in combination with a tissue attachment promoting material. Preferred instruments, devices, and/or implants are those utilized in minimally invasive spinal surgery. Suitable instruments include trocars, cannulas, expandable cannulas, endoscopes, rongeurs, curettes, trephines, catheters, scalpels, clamps, sponges, rotary cutters, guide sleeves, vertebral body distractors, resectors, retractors, guide wires, and any other instrumentation that contacts body tissue and may cause trauma. Suitable medical devices and implants include, for example, fusion cages, (lumbar and cervical), cervical and lumbar plates, rods, screws, hooks, anchors, fasteners, ligaments, nucleus replacement devices, intramedullary nails, clamps, facet arthroplasty devices, distraction balloons, facet spacers, intervertebral spacers, cautery devices, bovie, swabs, and the like.

Promoting tissue healing typically includes promoting the wound healing process, while preventing adverse wound healing affects such as scarring and adhesion formation. Adhesions are scar tissues that can be formed as a natural response to tissue trauma due in part to the surgical procedure. As the tissue heals, fibrin is deposited in the traumatized area. Fibrin is a known component that glues or "adheres" adjacent tissues together during tissue growth or vascularization. As a consequence, the fibrin deposits that are not replaced by normal tissues will result in permanent adhesions that remain in the body. These adhesions can prevent articulation of articulating components, cause dislocation of implants, and cause inflammation of nerves and consequently severe pain.

In addition to providing an anti-adhesion or anti-scarring effect, tissue healing promoting treatments also may include beneficial additives such as anti-inflammatory agents, analgesics, antibiotics, antiretroviral agents, immunosuppressive agents, and the like. These agents will aid in the healing process, as well as prevent implant or medical device rejection, and reduce pain associated with the trauma of the surgery.

Other tissue healing promoting agents include those that assist in growth of new tissue, such as vascular, muscular, tendon, cartilage, and bony tissue. These tissue healing promoting agents preferably are used in combination with the anti-adhesion and other agents discussed immediately above.

Preferably, the tissue healing promoting agents are present on at least a surface of a medical implement used in spinal surgery, whereby the anti-adhesion agents are capable of diffusing or otherwise releasing from the implement into the surrounding tissue. The agents preferably diffuse or release from the surface in the presence of natural body fluids, although fluid or energy may be applied to the surface of the implement during surgery to release the tissue healing promoting agents. When released, the tissue healing promoting agents can exist in a sustained release formulation such as included with a polymer capable of sustained release, or the agents exist as native compounds providing an immediate tissue healing promotion effect. Those skilled in the art will be capable of designing a suitable tissue healing promoting formulation for use in accordance with the embodiments, using the guidelines provided herein.

A preferred tissue healing promoting agent is an anti-adhesion agent. Anti-adhesion agents useful in the embodiments include any of the known anti-adhesion agents, or those later discovered, that are capable of reducing, ameliorating, or preventing the formation of adhesions after tissue trauma. Anti-adhesion agents can be in any form suitable for coating or impregnation on at least a portion of a surface of a medical implement. Typically, these agents are present as a bioresorbable barrier material in the form of a gel, a coating, fabric, film, and the like, and usually are released from the medical implement such that they are positioned between a healing post-surgical site and adjacent surrounding tissue. Examples of such barrier materials can be found in U.S. Pat. Nos. 5,412,068, 5,795,584, 6,034,140, 6,133,325, 6,136,333, and U.S. Patent Application Publication No. 2004/0115241, the disclosures of each of which are expressly incorporated herein by reference in their entireties.

The antiadhesion agents can be present as a bioresorbable medical device or polycarbonate fiber, copolymers and/or block copolymers derived from trimethylene carbonate, anti-adhesion membranes made of carboxyl-containing polysaccharides and polyethers, such as glucosamine, polymeric anti-adhesion compositions comprising poly(ester)/poly(oxyalkylene) ABA triblocks or AB diblocks. Similarly, the problem of foreign body reactions has been addressed by applying biocompatible polymeric coatings to medical devices, such as, for instance, stents. An exemplary method for coating a stent is disclosed in U.S. Pat. No. 6,153,252, the disclosure of which is expressly incorporated herein by reference in its entirety. Any of these agents can be used to coat or impregnate at least a portion of the surface of a medical implement that is used in spinal surgery, and preferably, those used in minimally invasive spinal surgical procedures.

Polyethylene glycol (PEG) in a variety of forms is a useful anti-adhesion agent in the embodiments disclosed herein. Useful agents are described in, for example, U.S. Pat. Nos. 6,410,044, 6,156,345, 6,007,833, 6,596,267, 6,696,499, 5,711,958, 6,743,521, 6,034,088, 5,931,165, 6,312,725, 6,458,889, 6,689,374, 6,685,956, 6,566,345, 6,673,361, 6,317,275, 5,583,114, 6,780,427, 6,743,521, 6,696,499, 6,689,903, 6,613,432, 6,602,975, 6,656,345, 6,551,610, 6,548,081, 6,534,591, 6,531,147, 6,413,539, 6,410,645, 6,410,044, 6,399,264, 6,391,939, 6,372,256, 6,352,710, 6,350,527, 6,312,725, 6,306,922, 6,217,894, 5,846,530, 5,795,584, 5,508,036, 4,603,695, and 4,346,108, the disclosures of each of which are incorporated by reference herein in their entireties. The PEG-based anti-adhesion agents can be present in a liquid formulation, as a gel, or as a film that can be applied or other supplied to at least a portion of the surface of a medical instrument, medical device, and/or medical implant. The gels, films, or barrier materials can exist on at least a portion of the medical implement, and be designed to release from the surface Other anti-adhesion agents suitable for use as the tissue healing promoting agent include synthetic anti-adhesion agents. Synthetic anti-adhesion agents include, for example, alkyd polyesters disclosed in U.S. Patent Publication No. 2004/0126420, materials derived from polyvinyl alcohols disclosed in U.S. Patent Publication No. 2003/0180251, polyhydroxyalkanoate polymers disclosed in U.S. Pat. No. 6,746,685, polyoxyalkylene compositions containing polyethylene oxide (PEO) disclosed in U.S. Pat. Nos. 6,436,425 and 6,746,485, fluorocarbons disclosed in U.S. Pat. No. 6,235,796, and the polymers disclosed in U.S. Pat. Nos. 6,280,745, and 6,031,069, the disclosures of all publications and patents incorporated by reference herein in their entireties.

The tissue healing promoting agents also may include natural anti-adhesion agents based on one or more of the following: alginates, cellulose, chitosan, collagen, fibrinogen/fibrin, hyaluronic acid, lactides, phospholipids, polysaccharides, and the like. Preferred alginates include a cross-linked alginate film placed at the site of trauma, or an aqueous solution of alginate, chitoasn and complexing agent to form a barrier, as respectively disclosed in U.S. Pat. Nos. 6,693,089, and 6,150,581, the disclosures of which are incorporated by reference herein in their entireties. Suitable cellulose-based anti-adhesion agents include sodium carboxymethyl cellulose, methyl cellulose, carboxymethyl cellulose, (CMC) cellulose acetate, mixtures of CMC and PEO, oxidized cellulose, fabrics comprised of oxidized regenerated cellulose, optionally having heparin absorbed thereon. These cellulose-based anti-adhesion agents are disclosed in U.S. Pat. Nos. 4,840,626, 5,007,916, 5,134,229, 5,156,839, and United States Patent Publication Nos. 2003/0073663 and 2003/0124087, the disclosures of which are incorporated by reference herein in their entireties.

Preferred chitosan-based anti-adhesion agents include N,O-carboxymethylchitosan (NOCC), chitosan and an immobilized polysaccharide, and covalent compositions of NOCC that may be intra or intermolecularly linked, as disclosed in U.S. Pat. Nos. 5,679,658 and 6,486,140, and WO 98/50050, the disclosures of which are incorporated by reference herein in their entireties. Any of the known collagen-based anti-adhesion agents and compositions can be used in the embodiments. Exemplary collagen-based anti-adhesion agents and compositions include, for example, patches including collagenous material, collagen monomers modified with an acylating agent or sulfonating agent, fibrillar collagen monomers modified with an acylating agent, sulfonating or combination, heparanized collagen, polymers of select analogs of proline, and mixtures thereof. Collagen-based anti-adhesion agents are disclosed in U.S. Pat. Nos. 6,599,526, 5,874,537, 5,219,895, 4,704,131, and 4,672,031, the disclosures of which are incorporated by reference herein in their entireties.

Preferred fibrinogen or fibrinogen/fibrin-based anti-adhesion agents and compositions include fibrinogen, a fibrinogen preparation containing a non-plasmin-acting fibrinolysis inhibitor such as eglin, fibrinogen and thrombin, fibrinogen, chaotropic substance and thrombin, fibrin polymer, sealant including fibrin monomer, a fibrinolysis-inhibiting protein, and a non-enzymatic polymerizing agent, fibrin or fibrinogen and a biodegradable and biocompatible polymer, cross-linked fibrin, and mixtures thereof. Suitable fibrinogen and fibrin-based anti-adhesion agents and compositions are disclosed in U.S. Patent Application Publication Nos. 2004/0043016, 2004/0009917, 2003/0133928, and 2002/0001584, and in U.S. Pat. Nos. 6,613,325, 6,492,494, 6,440,427, 6,074,663, and WO 00/72856, the disclosures of which are incorporated by reference herein in their entireties.

Hyaluronic acid is a viscous mucopolysaccharide found in animal and human tissues such as the umbilical cord, vitreous humor, synovial fluid, blood vessel walls and other connective tissues. The polysaccharide consists of repeating disaccharide units made of alternating D-glucuronic acid and N-acetyl-D-glucosamine residues, and possesses a molecular weight ranging from about 40,000 to 8,000,000 depending on the source and methods of extraction. Preferred hyaluronic acid-based anti-adhesion agents and compositions include cross-linked hyaluronic acid-protein biocomposites, esterified derivatives of hyaluronic acid, cross-linked derivatives of hyaluronic acid, the reaction product of hyaluronic acid and carbodiimide, hyaluronic acid gels with mannose-6-phosphate suspensions, high molecular weight hyaluronic acid, non-steroidal anti-inflammatory drugs (NSAIDs) and an organometallic salt, hyaluronic acid and dextran, and mixtures thereof. Suitable hyaluronic acid anti-adhesion agents and compositions are disclosed in U.S. Patent Publication No. 2003/0100739, and in U.S. Pat. Nos. 6,723,709, 6,630,167, 6,537,979, 6,521,223, 6,096,727, 6,093,388, 6,037,331, 5,358,973, 5,190,759, and WO 02/17853, the disclosures of which are incorporated by reference herein in their entireties. Hyaluronic acids are particularly preferred for use in the embodiments described herein.

Preferred lactide-based anti-adhesion agents and compositions include membranes constructed of polylactide resorbable polymers, a copolymer of caprolactone or methylene carbonate and lactide, lactide polymers, and the like. These lactide-based anti-adhesion agents are disclosed in U.S. Patent Application Publication No. 2004/0115241, and U.S. Pat. Nos. 6,673,362, and 5,962,006, the disclosures of which are incorporated by reference herein in their entireties. Preferred polysaccharide-based anti-adhesion agents and compositions include zwitterionic polysaccharides, activated and cross-linked polysaccharides, polysaccharide copolymer resins, compositions containing polysaccharides, CMC, hyaluronic acid or carboxymethylamylose, a gel made by reacting polyanionic polysaccharide with an activating agent, a gel made by reacting polyanionic polysaccharide with divinyl sulfone, polysaccharides in combination with low molecular weight peptide-based thrombin inhibitors, compositions comprising intermacromolecular complexes of carboxyl-containing polysaccharides and polyethers, compositions including the reaction product of a polyanionic polysaccharide with carbodiimide, polysaccharides grafted with antioxidants, cross-linked polysaccharide with a chemically induced charge, and dextrin. Particularly preferred polysaccharides are disclosed in U.S. Patent Application Publication Nos. 2004/0092433, 2003/0094719, 2003/0069354, and U.S. Pat. Nos. 6,703,041, 6,610,669, 6,521,223, 6,174,855, 6,133,325, 6,030,958, 5,612,321, and 5,502,042, and WO 99/581686, the disclosures of which are incorporated by reference herein in their entireties.

The formulations useful in the embodiments preferably include one or more of the tissue healing promoting treatments, and optionally include a tissue attachment promoting formulation. Such a composition provides a combined anti-adhesion effect and tissue healing and growth-promoting effect. Accordingly, to the extent tissue was resected from the surgical area and needs to be regenerated, the combination of a tissue healing promoting agent, like an anti-adhesion agent, together with a tissue attachment promoting agent, or growth promoting agent, like a growth factor, will provide a superior healing effect, when compared to the use of either agent alone. In addition to the tissue healing and tissue attachment promoting agents, the coatings may further comprise beneficial additives that aid in the healing process, such as antibiotics, antiretroviral drugs, anti-inflammatory agents, analgesics, immunosuppressive agents, and the like.

The tissue healing promoting treatment preferably includes antibiotics and antiretroviral drugs, in addition to the anti-adhesion agents. As discussed by Vehmeyer et al., the possibility exists that bacterial contamination can occur, for example, due to the introduction of contaminated allograft tissue from living donors. Vehmeyer, S B, et al., *Acta Orthop Scand.,* 73(2): 165-169 (2002). Antibiotics and antiretroviral drugs may be administered to prevent infection by pathogens that are introduced to the patient during implant surgery. Also, administration of antibiotics and antiretroviral drugs may be useful to account for nosocomial infections or other factors specific to the location where the implant surgery is conducted. Antibiotics and antiretroviral drugs useful in the tissue attachment promoting formulations include, but are not limited to, aminoglycosides such as tobramycin, amoxicillin, ampicillin, azactam, bacitracin, beta-lactamases, beta-lactam (glycopeptide), biomycin, clindamycin, chloramphenicol, chloromycetin, cefazolin, cephalosporins, ciprofloxacin, erythromycin, fluoroquinolones, gentamicin, macrolides, metronidazole, neomycin, penicillins, polymycin B, quinolones, rapamycin, rifampin, streptomycin, sulfonamide, tetracyclines, trimethoprim, trimethoprim-sulfamethoxazole, vancomycin, and mixtures and combinations thereof.

The tissue healing promoting treatment optionally may further comprise immunosuppressive agents, particularly in circumstances where an implant comprising an allograft composition or non-natural implant is delivered to the patient. Suitable immunosuppressive agents that may be administered in combination with the tissue attachment promoting formulations include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the tissue healing promoting agents include, but are not limited to, prednisolone, methotrexate, thalidomide, methoxsalen, rapamycin, leflunomide, mizoribine (bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

The tissue healing promoting treatment optionally comprises substances that enhance isotonicity and chemical stability. Such materials are non-toxic to patients at the dosages and concentrations employed, and include buffers such as phosphate, citrate, succinate, acetic acid, and other organic acids or their salts; antioxidants such as ascorbic acid; low molecular weight (less than about ten residues) polypeptides such as polyarginine and tripeptides; proteins such as serumalbumin, gelatin, and immunoglobulins; amino acids such as glycine, glutamic acid, aspartic acid, and arginine; monosaccharides, disaccharides, and other carbohydrates including cellulose and its derivatives, glucose, mannose, and dextrans; chelating agents such as EDTA; sugaralcohols such as mannitol and sorbitol; counterions such as sodium; nonionicsurfactants such as polysorbates, poloxamers, and polyethylene glycol PEG; and mixtures and combinations thereof.

Tissue healing promoting treatments useful for promoting the attachment of endogenous tissues may comprise bone morphogenetic factors. Bone morphogenetic factors are growth factors whose activity is specific to bone tissue including, but not limited to, demineralized bone matrix (DBM), bone protein (BP), bone morphogenetic protein (BMP), and mixtures and combinations thereof. Methods for producing DBM are well known in the art, and DBM may be obtained following the teachings of O'Leary et al. (U.S. Pat. No. 5,073,373) or by obtaining commercially available DBM formulations such as, for example, AlloGro® (commercially available from AlloSource, Centennial, Colo.). Additionally, formulations for promoting the attachment of endogenous bone may comprise bone marrow aspirate, bone marrow concentrate, and mixtures and combinations thereof. Methods of obtaining bone marrow aspirates as well as devices facilitating extraction of bone marrow aspirate are well known in the art and are described, for example, by Turkel et al. in U.S. Pat. No. 5,257,632, the disclosure of which is incorporated by reference herein in its entirety.

The tissue healing promoting treatment formulations may comprise osteoinductive and osteoconductive agents. While these agents may be used alone, it is preferred to use such osteoinductive and/or osteoconductive agents in combination with the anti-adhesion agents. Suitable osteoinductive and/or osteoconductive agents include, but are not limited to members of the families of Bone Morphogenetic Proteins (BMPs), Osteoprotegerin or any of the other osteoclastogenesis inhibitors, Connective Tissue Growth Factors (CTGFs), Vascular Endothelial Growth Factors (VEGFs), Transforming Growth Factor-betas (TGF-bs), Growth Differentiation Factors (GDFs), Cartilage Derived Morphogenic Proteins (CDMPs), and Lim Mineralization Proteins (LMPs).

BMPs are a class of proteins thought to have osteoinductive or growth-promoting activities on endogenous bone tissue, or function as pro-collagen precursors. Known members of the BMP family that may be utilized as osteoinductive agents in tissue attachment formulations include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18 polynucleotides and polypeptides, as well as mature polypeptides and polynucleotides encoding the same. The BMPs may be utilized as full length BMPs or fragments thereof, or combinations or mixtures thereof, or as polypeptides or polynucleotides encoding the polypeptide fragments of all of the recited BMPs.

Osteoclastogenesis inhibitors inhibit bone resorption by osteoclasts of the bone tissue surrounding the site of implantation. Osteoclast and Osteoclastogenesis inhibitors include, but are not limited to, Osteoprotegerin polynucleotides and polypeptides, as well as mature Osteoprotegerin polypeptides and polynucleotides encoding the same. The Osteoprotegerin protein specifically binds to its ligand, osteoprotegerin ligand (TNFSF11/OPGL), both of which are key extracellular regulators of osteoclast development. Osteoclastogenesis inhibitors further include, but are not limited to, chemical compounds such as bisphosphonate, 5-lipoxygenase inhibitors such as those described in U.S. Pat. Nos. 5,534,524 and 6,455,541 (herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (herein incorporated by reference in their entireties), sulfonamide derivatives such as those described in U.S. Pat. No. 6,313,119 (herein incorporated by reference in its entirety), and acylguanidine compounds such as those described in U.S. Pat. No. 6,492,356 (herein incorporated by reference in their entireties).

CTGFs are a class of proteins thought to have growth-promoting activities on connective tissues. Known members of the CTGF family include, but are not limited to, CTGF-1, CTGF-2, and CTGF-4, any of which may be incorporated into the tissue healing promoting treatments of the embodiments, in addition to polypeptides and polynucleotides encoding the same.

VEGFs are a class of proteins thought to have growth-promoting activities on vascular tissues. Known members of the VEGF family include, but are not limited to, VEGF-A, VEGF-B, VEGF-C, VEGF-D and VEGF-E, any of which may be incorporated into the tissue healing promoting treatments of the embodiments, in addition to polypeptides and polynucleotides encoding the same.

TGF-bs are a class of proteins thought to have growth-promoting activities on a range of tissues, including connective tissues. Known members of the TGF-b family include, but are not limited to, TGF-b-1, TGF-b-2, and TGF-b-3, any of which may be incorporated into the tissue healing promoting treatments of the embodiments, in addition to polypeptides and polynucleotides encoding the same.

Known GDFs include, but are not limited to, GDF-1, GDF-2, GDF-3, GDF-7, GDF-10, GDF-11, and GDF-15. GDF-1 polynucleotides and polypeptides correspond to GenBank Accession Numbers M62302, AAA58501, and AAB94786; GDF-2 polynucleotides and polypeptides correspond to GenBank Accession Numbers BC069643, BC074921, Q9UK05, AAH69643, and AAH74921; GDF-3 polynucleotides and polypeptides correspond to GenBank Accession Numbers AF263538, BC030959, AAF91389, AAQ89234, and Q9NR23; GDF-7 polynucleotides and polypeptides correspond to GenBank Accession Numbers AB 158468, AF522369, AAP97720, and Q7Z4P5; GDF-10 polynucleotides and polypeptides correspond to GenBank Accession Numbers BC028237 and AAH28237; GDF-11 polynucleotides and polypeptides correspond to GenBank Accession Numbers AF100907, NP_005802 and O95390; and GDF-15 polynucleotides and polypeptides correspond to GenBank Accession Numbers BC008962, BC000529, AAH00529, and NP_004855.

Known CDMPs and LMPs include, but are not limited to, CDMP-1, CDMP-2, LMP-1, LMP-2, and LMP-3. CDMP-1 polynucleotides and polypeptides correspond to GenBank Accession Numbers NM_000557, U13660, NP_000548 and P43026; CDMP-2 polypeptides correspond to GenBank Accession Numbers and P55106; LMP-1 polynucleotides and polypeptides correspond to GenBank Accession Numbers AF345904 and AAK30567; LMP-2 polynucleotides and polypeptides correspond to GenBank Accession Numbers AF345905 and AAK30568; and LMP-3 polynucleotides and polypeptides correspond to GenBank Accession Numbers AF345906 and AAK30569.

Other osteoinductive and osteoconductive factors, agents, and compounds such as hydroxyapatite (HA), tricalcium phosphate (TCP), collagen, fibronectin (FN), osteonectin (ON), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, insulin-like growth factor (IGF-1), platelet derived growth factors (PDGF), and fibroblast growth factors (FGF, bFGF, etc.) also may be included in the tissue healing promoting treatments.

Some of the tissue grwoth-promoting compounds described herein may be polypeptide compositions, which may be delivered by gene therapy vectors harboring the polynucleotides encoding the polypeptide of interest. The vector may be, for example, a phage, plasmid, viral, or retroviral vector. The gene therapy vectors may be included only in portions of the implant where tissue attachment is desired. Gene therapy methods require a polynucleotide which codes for the desired polypeptide and any other genetic elements necessary for the expression of the polypeptide by the target tissue. Such gene therapy and delivery techniques are known in the art. See, for example, International Publication No. WO 90/11092, which is herein incorporated by reference. Gene therapy vectors further comprise suitable adenoviral vectors including, but not limited to, those described in Kozarsky and Wilson, *Curr. Opin. Genet. Devel.,* 3:499-503 (1993); Rosenfeld et al., Cell, 68:143-155 (1992); Engelhardt et al., *Human Genet. Ther.,* 4:759-769 (1993); Yang et al., *Nature Genet.,* 7:362-369 (1994); Wilson et al., *Nature,* 365:691-692 (1993); and U.S. Pat. No. 5,652,224; which is herein incorporated by reference in its entirety.

Suitable gene therapy vectors include gene therapy vectors that do not integrate into the host genome and gene therapy vectors that integrate into the host genome. A desired polynucleotide also may be delivered in plasmid formulations. Plasmid DNA or RNA formulations refer to polynucleotide sequences encoding osteoinductive polypeptides that are free from any delivery vehicle that acts to assist, promote, or facilitate entry into the cell, including viral sequences, viral particles, liposome formulations, lipofectin or precipitating agents and the like.

Tissue healing promoting treatment agent polypeptides also may be available as heterodimers or homodimers, as well as multimers or combinations thereof. Recombinantly expressed proteins may be in native forms, truncated analogs, muteins, fusion proteins (e.g., fusion proteins with the FC portion of human IgG), and other constructed forms capable of inducing bone, cartilage, or other types of tissue formation as demonstrated by in vitro and ex vivo bioassays and in vivo implantation in mammals, including humans. Examples of preferred fusion proteins include, but are not limited to, ligand fusions between mature osteoinductive polypeptides and the FC portion of human Immunoglobulin G (IgG). Methods of making fusion proteins and constructs encoding the same are well known in the art.

Polypeptide compositions include, but are not limited to, full length proteins, fragments, and variants thereof. In a preferred embodiment, polypeptide fragments suitable for use in the tissue healing promoting treatment compositions are propeptide forms of the isolated full length polypeptides. In a particularly preferred embodiment, polypeptide fragments suitable for use in the tissue healing promoting treatment compositions are mature forms of the isolated full length polypeptides. Also preferred are the polynucleotides encoding the propeptide and mature polypeptides of the tissue attachment promoting agents. Preferred embodiments of variant tissue healing promoting agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Patent No. 0,401,384 as examples of methods of generating pegylated polypeptides). Embodiments further contemplate the use of polynucleotides and polypeptides having at least 95% homology, more preferably 97%, and even more preferably 99% homology to the isolated polynucleotides and polypeptides provided herein.

Other compounds that may be included in the tissue healing promoting formulations include platelet derived growth factor (PDGF); insulin-related growth factor-I (IGF-I); insulin-related growth factor-II (IGF-II); fibroblast growth factor (FGF); beta-2-microglobulin (BDGF II); biocidal/biostatic sugars such as dextran and glucose; peptides; nucleic acid and amino acid sequences such as leptin antagonists, leptin receptor antagonists, and antisense leptin nucleic acids; vitamins; inorganic elements; co-factors for protein synthesis; hormones; endocrine tissue or tissue fragments; synthesizers; enzymes such as collagenase, peptidases, and oxidases; polymer cell scaffolds with parenchymal cells; angiogenic agents; antigenic agents; cytoskeletal agents; cartilage fragments; living cells such as chondrocytes, bone marrow cells, mesenchymal stem cells, natural extracts, genetically engineered living cells, or otherwise modified living cells; autogenous tissues such as blood, serum, soft tissue, and bone marrow; bioadhesives; periodontal ligament chemotactic factor (PDLGF); somatotropin; antitumor agents and chemotherapeutics such as cis-platinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; and salts such as strontium salt, fluoride salt, magnesium salt, and sodium salt.

Besides or in addition to the active tissue healing promoting agents and tissue growth promoting agents, the tissue healing promoting treatments may include physical transformation of the implant surface. For example, the creation of nano-scale surface features has been implicated as a promoter of biologic activity at the surface of medical implants. The creation of appropriately sized pores and surface roughening in general also has been implicated as a treatment for encouraging interaction between adjacent tissues and medical implants. Any applicable method can be used in order to effect a tissue growth promoting physical transformation of the implant or medical device or instrument surfaces, including, but not limited to, machining, grinding, grit blasting, chemical etching, chemical vapor deposition, physical vapor deposition, electric discharge processes, laser etching, and the application of textured surfaces (e.g., textured cladding secured by welding, bonding, mechanical fixation, etc.). These surface treatments preferably are used in combination with the tissue healing promoting agents discussed above.

In one particularly preferred embodiment, the tissue healing promoting formulation comprises a series of time dependent healing promoting agents and growth factors in a time dependent release formulation. For example, depending on the type of surgery and type of medical implements utilized, various tissue healing promoting agents, and growth factors may be beneficial, including anti-adhesion agents, vascular growth promoting factors, collagen stimulation agents, and bone growth promoting agents, each of which may be released at different times. Preferably, the particular components are encapsulated in a microcapsule using conventional microencapsulation techniques, such that they can be released at different periods of time (e.g., different biodegradable or release polymers used, or different amounts used to encapsulate or otherwise entrain the particular tissue healing promoting agent or tissue growth promoting agent). In a preferred embodiment, the tissue healing promoting formulation includes anti-adhesion agents, vascular growth promoting agents, osteoconductive and/or osteoinductive agents, and collagen/cartilage stimulation agents, each capable of being released a different times. Such a formulation will provide the requisite tissue healing and attachment treatment at the requisite time.

Methods of making such a tissue healing promoting formulation include combining the particular agent(s) with a sustained release polymer or biodegradable polymer having variable release rates. Alternatively, each agent may be combined with, or encapsulated by, a different polymer or other material capable of differential release of the agent. It is preferred that the anti-adhesion agents be released first, either just prior to or coincident with release of the vascular growth promoting agents, so it is preferred that these agents be combined or otherwise coupled or conjugated to a polymer capable of relatively quick release. Preferably, the collagen/cartilage stimulation agents are released after the anti-adhesion and vascular growth promoting agents or factors, and finally, the optional osteoconductive and/or osteoinductive agents can be release last. These osteoconductive and/or osteoinductive agents therefore can be combined or otherwise coupled or conjugated to a polymer capable of slower release than those utilized for the vascular growth promoting agents. Skilled artisans recognize that if bone growth is not desirable, then osteoconductive and/or osteoinductive agents would not be used in the formulation, as would be the case where no bone was disturbed, and/or no bone implant was used. Using the guidelines provided herein, and coupled with the knowledge of microencapsulation and delayed or sustained release formulation technology, those skilled in the art will be capable of designing a suitable time dependent release tissue healing promotion formulation in accordance with the preferred embodiments.

The tissue healing promoting treatments disclosed herein, including formulations of anti-adhesion agents and tissue growth promoting agents, may be applied to any given medical implement. Medical instruments, devices, and/or implants that are useful in embodiments may be produced from a wide variety of materials, to which tissue healing promoting treatments may be applied. It is preferred that the tissue healing promoting treatment is applied to at least a portion of the surface of the medical instrument, device, and/or implant, and more preferred that the tissue healing promoting treatment is applied to the entire tissue-contacting surface of the medical instrument, device, and/or implant. For example, the medical implements may be fabricated from medical plastics such polyvinyl chlorides, polypropylenes, polystyrenes, acetal copolymers, polyphenyl sulfones, polycarbonates, acrylics, silicone polymers, polyetheretherketone (PEEK), polyurethanes, polyethylenes, polyethylene terphalate (PET), polymethylmethacrylate (PMMA), fabric, cotton, and mixtures and combinations thereof. Medical metals and metal alloys such as titanium, titanium alloys, tantalum, tantalum alloys, stainless steel alloys, cobalt-based alloys, cobalt-chromium alloys, cobalt-chromium-molybdenum alloys, niobium alloys, zirconium alloys, and shape memory alloys such as nitinol also may be used to fabricate the medical instruments, devices and implants. Additionally, ceramics such as alumina, zirconia, hydroxyapatite, calcium phosphate, and PCDC may be used. Also, natural substrates such as allograft, xenograft, and autograft tissues may be used to fabricate the medical implements. Medical implements useful in the embodiments may also be composites of medical plastics, metals, alloys, ceramics, and natural tissues, particularly composites comprising carbon fibers or hydroxyapatite polymers.

Methods for producing medical implements are well known in the art and are largely dictated by the particular instrument, device or implant that will be used. For example, general methods of manufacturing medical instruments devices, and implants with porous or roughened surfaces are well known in the art, for example, through the use of sintering beads, machining of device surfaces, laser etching of surfaces, using nanotube technology to create roughened surfaces, casting roughened surfaces, and chemically etching roughened surfaces.

In a preferred embodiment, the medical implements have porous surfaces because the pores may function as reservoirs for formulations of tissue healing promoting compounds and agents. After coating, however, the medical implement preferably is smooth and lubricious to facilitate insertion and extraction from the surgical site, especially when the implement is a surgical instrument that is intended to be introduced and withdrawn from the patient. It also is preferred that the tissue healing promoting compounds and agents be present at or near the surface of the medical implement such that, when contacted with surrounding tissue, or when inserted in the patient, the effective healing promoting and growth promoting agent(s) (and other optional agents present in the tissue healing promoting formulation) are released to the surrounding tissue and remain there after explantation of the medical instrument or device. The tissue healing promoting formulations may be released as chemical entities, or as a layer or releasable film from the medical implement. In an embodiment of the invention, medical implements having a porous surface on at least a portion thereof are impregnated with tissue healing promoting formulation only at surfaces of the instrument, device, and/or implant that will contact tissue or bone.

Embodiments also include methods of making the medical implements that include forming the implement, and then modifying at least a portion of its surface to provide a tissue healing promoting treatment on at least a portion of its surface. A preferred method involves forming an instrument, device, or implant such that it has a porous surface on at least a portion thereof, and subsequently contacting the porous surfaces of the instrument, device, or implant with an applicable tissue healing promoting formulation. The tissue healing promoting formulations may be applied to the medical implement using any of a number of methods, such as by spraying, painting, or brushing the formulation onto the medical implement or immersing the medical implement in a solution comprising the tissue healing promoting formulation.

Another embodiment of the invention contemplates a kit that includes the medical implement, or a plurality of such surgical implements described herein. It is preferred that the medical implement be packaged in a sterile container with a tissue healing promoting formulation already coated on at least a portion of its surface. Other components or agents useful in the tissue healing promoting formulation (e.g., growth promoting factors, antibiotics, anti-inflammatory agents, and the like) may be previously coated on the medical implement, or packaged separately with the medical implement that has been coated with the tissue healing promoting agent, such as an anti-adhesion agent. Then, if desired, the surgeon can apply the remainder of the tissue healing promoting formulation to the medical implement, just prior to, during, or after the surgery.

The medical implement alternatively may be packaged without the tissue healing promoting formulations, such as for example where the medical implement comprises a porous substrate into which the tissue healing promoting formulations may be subsequently impregnated. In such a situation, tissue healing promoting formulations generally may be placed into separate containers having sterile access ports such as a solution bag or vial having a stopper pierceable by a hypodermic injection needle. In a further embodiment, tissue healing promoting formulations may be stored in separate containers, for example, sealed ampoules or vials, as aqueous solutions or as lyophilized formulations for reconstitution. As an example of a lyophilized formulation, 10-ml vials may be filled with 5 ml of a sterile-filtered 1% (w/v) aqueous tissue healing promoting formulation, and the resulting mixture is lyophilized. The tissue healing promoting formulations may be prepared by reconstituting the lyophilized agent prior to administration in an appropriate solution, and then administering the formulation to the medical instrument, device, or implant prior to, concurrent with, or after surgery.

As one of skill in the art will recognize, the concentrations of tissue healing promoting agents may be variable based on the desired length or degree of action of the agents. Similarly, one of skill in the art will recognize that the tissue healing promoting compounds and agents may be in immediate release formulations or sustained release formulations optionally providing a time dependent release of the agents contained therein. Sustained release formulations are designed to provide tissue healing promoting agents at relatively consistent concentrations in bioavailable form over extended periods of time. Time dependent release formulations are designed to provide release of the particular agents at different periods of time.

In one embodiment, the tissue healing promoting agents are associated with biodegradable sustained release polymers. The biodegradable sustained release polymers may be used to selectively coat surfaces of the instruments, devices, and/or implants. Preferably, the biodegradable sustained release polymers are capable of diffusing out of the coating, or otherwise releasing from the surface (preferably the tissue-contacting surface) of the instrument, device or implant when implanted into a patient. Release can be effected either naturally by virtue of the presence of bodily fluids, body temperature, etc., or the polymers may be released by use of external release means, such as addition of water, saline, heat, light, irradiation, compression, air, and the like.

Alternatively, the biodegradable sustained release polymers may be used as cladding that is selectively attached to surfaces of the medical implement dependent upon whether tissue healing is or is not desired at an individual surface. Biodegradable sustained release polymers useful in sustained release formulations are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures thereof. The release profile of the biodegradable polymer can further be modified by inclusion of biostable polymers that influence the biodegradation rate of the polymer composition, including, but not limited to, silicones, polyesters, vinyl homopolymers and copolymers, acrylate homopolymers and copolymers, polyethers, and cellulosics.

Another method suitable of providing sustained release formulations that are useful for the delivery of tissue healing promoting agents in vivo and permit the initial burst of active agent to be controlled more effectively than previously possible is to conjugate the active agent with a water-insoluble biocompatible polymer and dissolve the resultant polymer-active agent conjugate in a biocompatible solvent to form a liquid polymer system similar to that described in U.S. Pat. Nos. 4,938,763, 5,278,201 and 5,278,202, the disclosures of which are incorporated by reference herein in their entireties. The water-insoluble biocompatible polymers may be those described in the above patents or related copolymers. In addition, the liquid polymer system also may include a water-insoluble biocompatible polymer that is not conjugated to the active agent. The water-insoluble biocompatible polymers then may be used to selectively coat surfaces of the instruments, devices, or implants dependent upon whether tissue healing is or is not desired at an individual surface.

Tissue healing promoting formulations that comprise active agents conjugated to biodegradable sustained release polymers or water-insoluble biocompatible polymers may be selectively impregnated in porous surfaces on the instrument, device, or implant, or they may be coated thereon using conventional coating techniques well known to those skilled in the art. Alternatively, formulations comprising active agents conjugated to polymers may be used to selectively coat surfaces of the medical implement. In this sense, the polymer formulations may be considered coatings or cladding on the medical implement's surfaces. In addition, membranes or films can be prepared that contain the tissue healing promoting formulations, and then shrink fit around the medical instrument, device, or implant, as described in U.S. Patent Application Publication No. 2004/0115241. These membranes or films can be designed to release as an entire membrane or film, or the release just the tissue healing promoting and optional tissue growth promoting agents, to the adjacent tissue when used during a surgical procedure. Finally, each active agent included in the tissue promoting formulation may be separately encapsulated, and then combined in one formulation and coated on or impregnated in the surface of the medical implement. A microencapsulated formulation is particularly suitable for use with medical swabs that can be used to swab the surgical site before, during, and/or after the surgery.

Methods of treatment of the surfaces of medical instruments, devices, or implants with tissue healing promoting formulations that have been described herein include providing a selectively porous medical implement surface, selectively impregnating the porous surfaces with the appropriate formulations, selectively coating medical implement surfaces with the appropriate formulations, and selectively attaching or applying cladding with the appropriate formulations to the implement surfaces. It should be understood that embodiments are not limited to a specific method of applying the tissue healing promoting formulations, but rather encompass all such applicable methods of applying the formulations. One of skill in the art will recognize still other methods, and all such methods are contemplated for use herein.

Embodiments also include methods of performing surgery, preferably minimally invasive surgery, and most preferably, minimally invasive spinal surgery, using the medical instruments, devices, and implants described herein. The methods typically include making at least one skin incision, accessing the surgical site using one or more medical instruments described herein, preparing the surgical site using one or more medical instruments and/or devices described herein, and optionally implanting a medical implant described herein. The surgical method further entails withdrawing the medical instruments and/or devices from the surgical site, releasing tissue healing promoting formulations described herein to the tissue adjacent the surgical site, and closing the at least one incision. Alternatively, the method includes the use of conventional surgical instruments to carry out the surgical procedure, withdrawing the medical instruments, and then swabbing the surgical site with a swab coated or impregnated with a tissue healing promoting formulation described herein. The surgical methods of the embodiments are less invasive, provide fewer adhesions and scarring, provide faster healing time, and provide greater surgical success, when compared to the identical surgeries carried out without using an instrument, device, and/or implant having at least one surface containing a tissue healing promoting treatment described herein.

An exemplary surgery could include accessing a vertebral body to perform a facet arthroplasty by serialing dilating tissue from a skin incision to a vertebral body using successively larger cannulas, each time dilating the tissue further. Further details on serial dilation are provided below with reference to the appended drawings. An access portal having a diameter within the range of from about 5 mm to about 30 mm can be prepared using this technique. Preferably, each cannula used in the dilation includes on at least one surface thereof, a tissue healing promoting treatment as described herein. Even more preferably, glucosamine is used as an anti-adhesion agent in the tissue healing promoting treatment formulation. After accessing the facet joint, an expandable facet spacer, preferably in the form of an inflatable balloon, then can be inserted through the access portal and inflated to distract or dilate the facet joint and reduce pain. It is preferred that that the expandable facet spacer be coated with a tissue healing promoting formulation, and more preferably, a formulation comprising glucosamine, an optional tissue growth promoting material, and at least one beneficial additive selected from an antibiotic, anti-inflammatory agent, immunosuppresive agent, or antiretroviral agent, or mixtures thereof. The instruments then can be removed and the wound closed.

Embodiments described herein have application to a wide range of surgical procedures, and particularly spinal procedures such as laminotomy, laminectomy, foramenotomy, facetectomy and discectomy. Prior surgical techniques for each of these procedures has evolved from a grossly invasive open surgeries to the minimally invasive techniques described above. However, in each of these minimally invasive techniques, tissue damage still occurs even using smaller instruments, devices, and implants, which sometimes leads to the formation of adhesions and scars. The medical instruments, devices, and implants of the embodiments described herein have a particularly preferred application in a surgical technique that permits each of these several types of surgical procedures to be performed via a single working channel in a minimally invasive manner. The embodiments also can be used from any approach and in other regions besides the spine. For instance, the embodiments contemplate apparatus, instruments, devices, and implants appropriately sized and treated for use in transnasal, transphenoidal and pituitary surgeries.

The procedures of a typical minimally invasive surgery utilizing a single working channel, or access port, are described with reference to FIG. 1. As can readily be seen from each of the depicted steps (a)-(i), the present embodiment permits a substantially mid-line or medial posterior approach to the spine. Of course, it is understood that many of the following surgical steps can be performed from other approaches to the spine, such as posterolateral and anterior. In a first procedure of the technique, a guidewire 150 can be advanced through the skin and tissue into the laminae M of a vertebral body V. The guidewire 150 preferably is coated with a tissue healing promoting formulation comprising at least an anti-adhesion agent, and preferably also comprising at least one of the beneficial additives described above.

Preferably, a small incision is made in the skin to facilitate penetration of the guidewire through the skin. In addition, most preferably the guidewire, which may be a K-wire, is inserted under radiographic or image guided control to verify its proper positioning within the laminae L of the vertebra V. It is, of course, understood that the guidewire 150 can be positioned at virtually any location in the spine and in any portion of a vertebra V. The positioning of the guidewire is dependent upon the surgical procedure to be conducted through the working channel or access port. Preferably, the guidewire 150 is solidly anchored into the vertebral bone, being tapped by a mallet if necessary. In this regard, it is preferred that the tip and bone penetrating surface of the guidewire 150 be coated with a tissue healing promoting formulation of the embodiments.

After placement of the guidewire 150, a series of tissue dilators are advanced over the guidewire 150, as depicted in (b)-(d) in FIG. 1. Alternatively, the dilators can be advanced through the incision without the aid of a guidewire, followed by blunt dissection of the underlying tissues. In the specific illustrated embodiment, a series of successively larger dilators 151, 152 and 153 are concentrically disposed over each other and over the guidewire 150 and advanced into the body to sequentially dilate the perispinous soft tissues.

Most preferably, the tissue dilators are of the type shown in FIG. 2. A dilator 130 preferably includes a hollow sleeve 135 defining a channel 131. The channel 131 allows the dilator 130 to be placed over a guidewire (shown in FIG. 1 as 150) or other dilators. The hollow sleeve 135 has a working end 136 defining a first opening 132 in communication with the channel 131 and an opposite end 137 defining a second opening 133. The working end 136 is tapered to a tapered tip 138 to atraumatically displace tissue. Preferably, a gripping portion 140 is provided on the outer surface 141 of the sleeve 135 adjacent the opposite end 137. In one embodiment, the gripping portion 140 is defined by a plurality of circumferential grooves 142 defined in the outer surface 141. The grooves 142 are configured for manual gripping of the dilator 130 to manipulate the dilator 130 through tissue. Preferably, the grooves 142 are partially cylindrical. In the embodiment shown in FIG. 2, the gripping portion 140 includes a number of circumferential flats 143 each of the circumferential grooves 142. The grooves 142 have a first width $W_1$ along the length of the sleeve 135 and the flats 143 have a second width $W_2$ 146 along the length. Preferably, the first and second widths $W_1$ and $W_2$ are substantially equal.

It is especially preferred that each tissue dilator be coated at least partially with a tissue healing promoting formulation containing an anti-adhesion agent, and preferably at least one of the beneficial additives disclosed above. Preferably, the tissue healing promoting formulation is coated or otherwise attached or absorbed in or at the surface of dilator 130 in areas where tissue healing would be needed the most. These areas are indicated, for example, by 144, 145 in FIG. 2. Alternatively, all of the external surface of dilator 130 could be coated with a tissue healing promoting formulation described herein. In a specific embodiment, the dilators have successively larger diameters, ranging from 5 mm, to 9 mm to 12.5 mm up to 20-25 mm for the largest dilator. Other dilator sizes are contemplated depending upon the anatomical approach and upon the desired size of the working channel.

In the next step of the illustrated technique, a working channel cannula 20 is advanced over the largest dilator 153, as shown in step (e), and the dilators and guidewire 150 are removed, as shown in step (f). Preferably, the working channel cannula 20 has an inner diameter $D_1$ of 12.7 mm so that it can be easily advanced over the 12.5 mm outer diameter of the large dilator 153. Working channel cannulas are contemplated depending upon the anatomical region and surgical procedure. Again, all or a portion of the tissue contacting surface of working channel cannula 20 is coated with a tissue healing promoting formulation described herein. It is preferred that longitudinal elements like cannula 20 and serial dilators 151, 152, 153, be contacted with a sheet comprising the tissue healing promoting formulation, and then heating the resulting sheet and cannula 20 to adhere the tissue promoting formulation to the surface thereof.

With the cannula 20 in position, a working channel or access port is formed between the skin of the patient to a working space adjacent the spine. It is understood that the length of the cannula 20 is determined by the particular surgical operation being performed and the anatomy surrounding the working space. For instance, in the lumbar spine the distance between the laminae M of a vertebra V to the skin of the patient requires a longer cannula 20 than a similar procedure performed in the cervical spine where the vertebral body is closer to the skin. In one specific embodiment in which the cannula 20 is used in a lumbar discectomy procedure, the cannula has a length within the range of from about 70 mm to about 100 mm, although generally only about half of the length of the cannula 20 will be situated within the patient during the procedure.

The working channel cannula 20 is at least initially only supported by the soft tissue and skin of the patient. The cannula 20 may include, for example, a mounting bracket 27 affixed to the outer surface of the cannula (FIG. 1(f)). This mounting bracket 27 can be fastened to a flexible support arm 160, which can be of known design. Preferably, the flexible support arm 160 is engaged to the bracket 27 by way of a bolt and wing nut 161, as shown in FIG. 1 (i), although other fasteners are also contemplated.

Once the cannula 20 is seated within the patient, a fixture 30 can be engaged over the proximal end of the cannula 20. Fixture 30 preferably provides an optics bore 60 for supporting an elongated viewing element, such as element 50 shown in FIG. 1(h). In accordance with the embodiments, the viewing element 50 is advanced into the fixture 30 and supported by an optics bore. In one specific embodiment, the element 50 is most preferably a fiber optic scope, although a rod lens scope, "chip on a stick" or other viewing scopes may be utilized. The viewing element 50 can be of a variety of types, including a rigid endoscope or a flexible and steerable scope. Preferably, the distal end of viewing element 50, to the extent it comes in contact with internal tissue or bone, is coated with a tissue healing promoting formulation of the embodiments described herein. In the final step (i) of the procedure shown in FIG. 1, the flexible arm 160 is mounted to the bracket 27 to support the cannula 20 which in turn supports the optical viewing element 50.

With the viewing element or scope 50 supported by the fixture 30, the surgeon can directly visualize the area beneath the working channel of the cannula 20. The surgeon can freely manipulate the viewing element 50 within the working channel or beyond the distal end of the cannula into the working space. In the case of a steerable tip scope, the distal end of the viewing element 50, which may carry a lens, can be manipulated to different positions. With virtually any type of viewing element, the manipulation and positioning of the scope is not limited by the working channel, in contrast to prior systems. This wanding back and forth of cannula 20 and viewing element 50 may cause damage to the surrounding tissue. Consequently, it is preferred that the distal end of cannula 20 is provided with a tissue healing promoting treatment as described herein.

Because the working channel cannula 20 is freely situated within the patient's skin and tissue, it can be manipulated so that the working space beneath the cannula 20 is more appropriately centered over the target region of the spine. Repositioning of the cannula 20 can be performed under fluoroscopic guidance. Alternatively, the cannula may be fitted with position sensing devices, such as LEDs, to be guided stereotactically. As the cannula is being repositioned, the surgeon can also directly visualize the spine through the viewing element 50.

Once the position of the cannula 20 is established and a working space is oriented over the proper target tissue, a variety of tools and instruments can be extended through the working channel 25 to accomplish the particular surgical procedure to be performed. For instance, in the case of a laminotomy, laminectomy, foramenotomy or facetectomy, a variety of rongeurs, curettes, and trephines can be extended through the working channel opening and through the working channel of the cannula 20 into the working space. Preferably, the working end of each medical instrument used in the surgical procedure is provided with tissue healing promoting treatment as described herein. Alternatively, only one or a small portion of the medical instruments that are used in the surgical procedure contain a tissue healing promoting treatment, and provide the requisite healing agents to the surrounding tissue.

It is understood that these various tools and instruments are designed to fit through the working channel. For instance, in one specific embodiment, the working channel through the cannula 20 can have a maximum diameter $d_2$ of 12.7 mm. However, with the viewing element 50 extending into the working channel, the effective diameter is about 8 mm in the specific illustrated embodiment, although adequate space is provided within the working channel around the viewing element 50 to allow a wide range of movement of the tool or instrument within the working channel. The embodiments are not limited to particular sizes for the working channel and effective diameter, since the dimensions of the components will depend upon the anatomy of the surgical site and the type of procedure being performed.

Preferably, each of the tools and instruments used with the working channel cannula 20 are designed to minimize obstruction of the surgeon's visualization of and access to the working space at the distal end of the working channel cannula. Likewise, the instruments and tools are designed so that their actuating ends which are manipulated by the surgeon are displaced from the working channel cannula 20.

The surgical procedures conducted through the working channel cannula 20 and within the working space at the distal end of the cannula can be performed "dry"—without the use of irrigation fluid, or "wet"—with irrigation fluid. Under some circumstances, the need for irrigation is less critical, such as when cutting operations are being performed by a power drill. It has been found in prior surgical procedures that the use of a power drill in a fluid environment can cause turbulence or cavitation of the fluid. This turbulence can completely shroud the surgeon's view of the surgical site at least while the drill is being operated. If a power drill is used, it is preferred that the drill bits used for cutting are coated or otherwise treated with a tissue healing promoting formulation that includes anti-adhesion agents, and osteoconductive or osteoinductive agents. It is especially preferred that that surgical procedures be conducted with irrigation, or "wet," whereby the irrigation fluid may assist in the release of the tissue healing promoting formulation coated on the exterior surface of one or more of the medical instruments, devices, and/or implants used in the surgical procedure. In this regard, separate irrigation and aspiration elements can also be inserted through the working channel as required by the procedure.

Once the working channel cannula 20 and the optics 50 are in position, as depicted in FIG. 1(*i*), the paraspinous tissue can be resected using instruments as described above, and a laminectomy performed using various rongeurs, curettes and drills. As necessary, the cannula 20 can be angled to allow a greater region of bone removal, which may be necessary for access to other portions of the spinal anatomy. In some instances, access to the spinal canal and the posterior medial aspects of the disc annulus may require cutting a portion of the vertebral bone that is greater than the inner diameter of the working channel 25. Thus, some manipulation of the cannula 20 may be necessary to permit removal of a greater portion of bone. In other operations, multi-level laminectomies or foramenotomies may be necessary. In this instance, these multi-level procedures can be conducted by sequentially inserting the working channel cannula 20 through several small cutaneous incisions along the spinal mid-line. Alternatively, several working channel cannulas 20 can be placed at each of the small cutaneous incisions to perform the multi-level bone removal procedures.

Again, in accordance with the preferred illustrated surgical technique, an opening is cut into the laminae M of the vertebra V providing direct visual access to the spinal canal itself. As necessary, tissue surrounding the spinal nerve root can be removed utilizing micro surgical knives and curettes. Once the spinal nerve root is exposed, a retractor can be used to gently move and hold the nerve root outside the working space. With the tissue retractor in place within the working channel, bone within the spinal canal, such as may occur in a burst fracture, can be removed with a curette or a high speed drill. Alternatively, fractured bone may be impacted back into the vertebral body with a bone impactor or an expandable compacting device, such as an expandable and preferably constrained balloon. At this point, if the spinal procedure to be performed is the removal of epidural spinal tumors, the tumors can be resected utilizing various micro-surgical instruments. In other procedures, the dura may be opened and the intradural pathology may be approached with micro-surgical instruments passing through the working channel cannula 20. In accordance with the specific illustrated technique, with the nerve root retracted posterior medial disc herniations can be readily excised directly at the site of the herniation.

If a spinal fusion or nucleus replacement device are to be implanted, a discectomy may be performed using the appropriate instrumentation, and the fusion cage or nucleus replacement device may be inserted through the cannula 20. If spinal fixation is desired, fixation elements such as plates, screws, rods, and the like can be passed through the cannula 20 and fixed in the appropriate area on the vertebral body. Each of the instruments, devices and/or implants preferably has at least a portion of its surface including a tissue healing promoting treatment in accordance with the embodiments described herein.

The foregoing detailed description is provided to describe the invention in detail, and is not intended to limit the invention. Those skilled in the art will appreciate that various modifications may be made to the invention without departing significantly from the spirit and scope thereof.

What is claimed is:

1. A medical implement selected from the group consisting of trocars, cannulas, expandable cannulas, endoscopes, rongeurs, curettes, trephines, catheters, scalpels, clamps, sponges, rotary cutters, guide sleeves, vertebral body distractors, rescetors, retractors, guide wires, fusion cages, cervical and lumbar plates, rods, screws, hooks, anchors, fasteners, ligaments, nucleus replacement devices, intramedullary nails, clamps, facet arthroplasty devices, distraction balloons, facet spacers, intervertebral spacers, cautery devices, bovie, and swabs; wherein the medical implement comprises a tissue healing promoting coating disposed on at least a portion of its surface, the tissue healing promoting coating comprising:
   (a) at least one anti-adhesion agent,
   (b) at least one beneficial additive selected from the group consisting of antibiotics, antiretroviral drugs, anti-inflammatory agents, analgesics, immunosuppressives, substances that enhance isotonicity and chemical stability, and mixtures thereof,
   (c) a tissue attachment or growth promoting agent, and
   (d) a collagen/cartilage stimulation agent,
   wherein the anti-adhesion agent is encapsulated in a first polymer, the beneficial additive is encapsulated in a second polymer, the tissue attachment or growth promoting agent is encapsulated in a third polymer, and the collagen/cartilage stimulation agent is encapsulated in a fourth polymer,
   wherein the first, second, third, and fourth polymers are capable of differential release of the anti-adhesion agent, beneficial additive, tissue attachment or growth promoting agent, and the collagen/cartilage stimulation agent, the fourth polymer being configured to release the collagen/cartilage stimulation agent after the at least one anti-adhesion agent is released from the first polymer; and wherein at least a portion of the surface of the medical implement includes nano-scale surface features configured to promote tissue growth.

2. The medical implement of claim 1, wherein the tissue healing promoting coating further comprises an osteoinductive agent or an osteoconductive agent, the osteoinductive agent or osteoconductive agent being encapsulated in a fifth polymer configured to release the osteoconductive agent or osteoinductive agent after the collagen/cartilage stimulation agent is released from the fourth polymer.

3. The medical implement of claim 1, wherein the anti-adhesion agent comprises polyethylene glycol.

4. The medical implement of claim 1, wherein the anti-adhesion agent comprises glucosamine.

5. The medical implement of claim 1, wherein the anti-adhesion agent comprises an agent selected from the group consisting of alkyd polyesters, polyvinyl alcohol, polyhydroxyalkanoate polymers, polyethylene oxide (PEO), fluorocarbons, and mixtures thereof.

6. The medical implement of claim 1, wherein the anti-adhesion agent is selected from the group consisting of alginates, chitosan, collagen, fibrinogen, hyaluronic acid, lactides, phospholipids, polysaccharides, and mixtures thereof.

7. The medical implement of claim 2, wherein the osteoconductive or osteoinductive agent is selected from the group consisting of one or more isolated osteoinductive agents selected from the group consisting of one or more Bone Morphogenic Proteins (BMPs), one or more Vascular Endothelial Growth Factors (VEGFs), one or more Connective Tissue Growth Factors (CTGFs), one or more Growth Differentiation Factors (GDFs), one or more Cartilage Derived Morphogenic Proteins (CDMPs), one or more Lim Mineralization Proteins (LMPs), one or more Transforming Growth Factor-betas (TGF-Ps), and any combination thereof.

8. The medical implement of claim 7, wherein the one or more isolated osteoinductive agents are selected from the group consisting of: a) BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, and any combination thereof; b) CTGF-1, CTGF-2, CGTF-3, CTGF-4, and any combination thereof; c) VEGF-A, VEGF-B, VEGF-C, VEGF-D, VEGF-E, and any combination thereof; d) GDF-1, GDF-2, GDF-3, GDF-7, GDF-10, GDF-11, GDF-15, and any combination thereof; e) CDMP-1, CDMP-2, LMP-1, LMP-2, LMP-3, and any combination thereof; f) TGF-P-1, TGF-a-2, TGF-P-3, and any combination thereof; and g) any combination of one or more members of these groups.

9. A method of performing a spinal surgery comprising: making an incision in the skin of a patient; accessing the surgical site using minimally invasive procedures; preparing the surgical site; optionally implanting a spinal implant at the surgical site; and closing the incision, whereby one or more of the procedures is carried out using the medical implement as claimed in claim 1.

10. The method of claim 9, wherein use of the medical implement results in release of tissue healing promoting formulations to the tissue adjacent the surgical site.

11. The method of claim 9, wherein accessing the surgical site comprises:
placing a guide wire through the incision to the surgical site; and serially dilating the patient's tissue using a series of consecutively larger diameter cannulas to prepare a channel to the surgical site, the channel capable of accepting surgical instruments useful in the surgery.

12. The method of claim 11, wherein the guide wire and each consecutively larger diameter cannula comprises a tissue healing promoting treatment on at least a portion of its surface, the tissue healing promoting treatment comprising at least an anti-adhesion agent.

13. The method of claim 9, wherein preparing the surgical site comprises expanding an expandable member coated with a tissue healing promoting treatment on at least a portion of its surface, the tissue healing promoting treatment comprising at least an anti-adhesion agent.

14. A kit comprising the medical implement of claim 1.

15. The kit of claim 14, wherein the tissue healing promoting coating and the medical implement are packaged separately.

16. A medical implement selected from the group consisting of trocars, cannulas, expandable cannulas, endoscopes, rongeurs, curettes, trephines, catheters, scalpels, clamps, sponges, rotary cutters, guide sleeves, vertebral body distractors, resectors, retractors, guide wires, fusion cages, cervical and lumbar plates, rods, screws, hooks, anchors, fasteners, ligaments, nucleus replacement devices, intramedullary nails, clamps, facet arthroplasty devices, distraction balloons, facet spacers, intervertebral spacers, cautery devices, bovie, and swabs; wherein the medical implement comprises a surface, wherein at least a portion of the surface is impregnated with a tissue healing promoting agent comprising:
(a) at least an anti-adhesion agent,
(b) at least one beneficial additive selected from the group consisting of antibiotics, antiretroviral drugs, anti-inflammatory agents, analgesics, immunosuppressives, substances that enhance isotonicity and chemical stability, and mixtures thereof,
(c) a tissue attachment or growth promoting agent, and
(d) a collagen/cartilage stimulation agent,
wherein the anti-adhesion agent is encapsulated in a first polymer, the beneficial additive is encapsulated in a second polymer, the tissue attachment or growth promoting agent is encapsulated in a third polymer, and the collagen/cartilage stimulation agent is encapsulated in a fourth polymer,
wherein the first, second, third, and fourth polymers are capable of differential release of the anti-adhesion agent, beneficial additive, tissue attachment or growth promoting agent and collagen/cartilage stimulation agent, the fourth polymer being configured to release the collagen/cartilage stimulation agent after the anti-adhesion agent is released from the first polymer; and
wherein at least a portion of the surface of the medical implement includes nano-scale surface features configured to promote tissue growth.

17. The medical implant of claim 1, wherein the anti-adhesion agent is selected from the group consisting of cellulose and fibrin.

18. The medical implement of claim 1 wherein the nano-scale surface features configured to promote tissue growth includes appropriately sized pores and/or surface roughening.

19. The medical implement of claim 16 wherein the nano-scale surface features configured to promote tissue growth includes appropriately sized pores and/or surface roughening.

20. The medical implant of claim 1, wherein the third polymer is configured to release the tissue attachment or growth promoting agent after or coincident with the release of the at least one anti-adhesion agent from the first polymer.

21. The medical implant of claim 16, wherein the third polymer is configured to release the tissue attachment or growth promoting agent after or coincident with the release of the anti-adhesion agent from the first polymer.

* * * * *

UNITED STATES PATENT AND TRADEMARK OFFICE
CERTIFICATE OF CORRECTION

PATENT NO. : 8,414,907 B2  
APPLICATION NO. : 11/116414  
DATED : April 9, 2013  
INVENTOR(S) : Molz et al.

Page 1 of 1

It is certified that error appears in the above-identified patent and that said Letters Patent is hereby corrected as shown below:

In the Specifications

In Column 2, Line 7, after "RE37,005," delete "U.S. Pat. Nos.".

In the Claims

In Column 22, Line 28, in Claim 1, delete "rescetors," and insert -- resectors, --, therefor.

In Column 22, Line 31, in Claim 1, after "nails," delete "clamps,".

In Column 23, Line 25, in Claim 7, delete "(TGF-Ps)," and insert -- (TGF-bs), --, therefor.

In Column 23, Line 32, in Claim 8, delete "CGTF-3," and insert -- CTGF-3, --, therefor.

In Column 23, Line 37, in Claim 8, delete "TGF-P-1, TGF-a-2, TGF-P-3," and insert -- TGF-β-1, TGF-β-2, TGF-β-3, --, therefor.

In Column 24, Line 15, in Claim 16, after "nails," delete "clamps,".

In Column 24, Line 37, in Claim 16, delete "agent and" and insert -- agent, and --, therefor.

In Column 24, Line 43, in Claim 17, delete "implant" and insert -- implement --, therefor.

In Column 24, Line 55, in Claim 20, delete "implant" and insert -- implement --, therefor.

In Column 24, Line 59, in Claim 21, delete "implant" and insert -- implement --, therefor.

Signed and Sealed this  
Fourth Day of June, 2013

Teresa Stanek Rea  
*Acting Director of the United States Patent and Trademark Office*